US012765879B2

(12) United States Patent
Gunuskey

(10) Patent No.: US 12,765,879 B2
(45) Date of Patent: Oct. 20, 2026

(54) LANYARD-BASED TOURNIQUET

(71) Applicant: Keith E. Gunuskey, Honesdale, PA (US)

(72) Inventor: Keith E. Gunuskey, Honesdale, PA (US)

( * ) Notice: Subject to any disclaimer, the term of this patent is extended or adjusted under 35 U.S.C. 154(b) by 17 days.

(21) Appl. No.: 19/076,394

(22) Filed: Mar. 11, 2025

(65) Prior Publication Data

US 2025/0302484 A1 Oct. 2, 2025

Related U.S. Application Data

(60) Provisional application No. 63/571,806, filed on Mar. 29, 2024.

(51) Int. Cl.

| | |
|---|---|
| ***A61B 17/132*** | (2006.01) |
| ***A45F 5/00*** | (2006.01) |
| ***A61B 17/00*** | (2006.01) |
| ***A61B 90/90*** | (2016.01) |

(52) U.S. Cl.

CPC .......... *A61B 17/1322* (2013.01); *A45F 5/155* (2025.01); *A61B 90/90* (2016.02); *A45F 2005/002* (2013.01); *A45F 2005/006* (2013.01); *A61B 2017/00367* (2013.01); *A61B 2017/00477* (2013.01)

(58) Field of Classification Search

CPC . A61B 17/132; A61B 17/135; A61B 17/1322; A61B 17/1327

See application file for complete search history.

(56) References Cited

U.S. PATENT DOCUMENTS

| | | | | |
|---|---|---|---|---|
| 11,547,423 B2 | 1/2023 | Peterson et al. | | |
| 11,684,373 B2 | 6/2023 | Parsons | | |
| 2005/0273134 A1* | 12/2005 | Esposito | A61B 17/1322 | 606/203 |
| 2014/0135819 A1* | 5/2014 | Brown | A61B 17/1327 | 606/203 |
| 2018/0168663 A1* | 6/2018 | Hill | A61B 17/1322 | |

* cited by examiner

*Primary Examiner* — Tuan V Nguyen
(74) *Attorney, Agent, or Firm* — Wendy W. Koba

(57) ABSTRACT

An emergency tourniquet is proposed to be formed out of a lanyard of the type used to carry an ID badge in many academic or institutional settings. The lanyard is configured to include a windlass (i.e., a small, rotatable rod) that may be used to apply a proper amount of pressure to stem the excessive flow of blood without cutting off the supply to extremities. When needed, a portion of the lanyard is passed through the included clip (used for ID attachment) to form a loop. The affected body part is then passed through the loop and the windlass rotated until a sufficient pressure is applied to stem the flow of blood. A releasable retainment element (e.g., hook-and-loop device) is included and surrounds the rotated windlass once the desired amount of pressure is applied to the body, ensuring that the pressure is retained until medical help arrives.

10 Claims, 5 Drawing Sheets

LANYARD-BASED TOURNIQUET

CROSS-REFERENCE TO RELATED APPLICATIONS

This applications claims priority from U.S. Provisional Application No. 63/571,806, filed Mar. 29, 2024 and herein incorporated by reference.

TECHNICAL FIELD

Disclosed herein is a lanyard that is particularly configured to function as a tourniquet in an emergency situation.

BACKGROUND OF THE INVENTION

There are known to be many different situations or locations where individuals are required to wear IDs in a visible manner. In many cases, the IDs are supported on a lanyard that an individual wears around his/her neck. In most academic settings (at least at the elementary and high school levels), teachers and other administrators wear lanyards bearing their ID on a daily basis. Many college students wear their IDs on a lanyard as well.

It is an unfortunate circumstance of today's world that emergency situations arise in academic or other institutional facilities where individuals are stabbed, cut, or otherwise injured. There is often an immediate need to control severe bleeding in these situations. In many cases, even if a first aid kit may be "somewhere" within a building where the injury has occurred, the ability to locate it in time to be of use is questionable.

SUMMARY OF THE INVENTION

The needs as described above are addressed by the present invention, which is directed to a lanyard as worn in many academic and business locations and, more particularly, to a lanyard that is particularly configured to function as a tourniquet in an emergency situation.

In accordance with the principles of the present invention, a lanyard is configured to include a windlass (i.e., a small, rotatable rod) that may be used to apply a proper amount of pressure to stem the excessive flow of blood without cutting off the supply to extremities.

Advantageously, the simple design of incorporating a windlass allows for the individual wearing the lanyard to utilize it as a tourniquet on him/herself until medical professionals arrive on the scene.

An exemplary embodiment of the present invention may take the form of an emergency tourniquet including a lanyard including a clip member attached thereto, a windlass rod, attachment means for securing the windlass rod to a section of the lanyard, and a releasable retaining element disposed on the lanyard in proximity to the windlass rod. When to be used as a tourniquet, a portion of the lanyard may be passed through the clip member to form a loop so as to be positioned over an injury requiring compression with the windlass rod rotated until a sufficient degree of compression is provided. The releasable retaining element is then positioned to cover the rotated windlass rod and secure it in a manner that maintains the sufficient degree of compression.

Other and further aspects and advantages of the present invention will become apparent during the course of the following discussion and by reference to the accompanying drawings.

BRIEF DESCRIPTION OF THE DRAWINGS

Referring now to the drawings, where like numerals represent like parts in several views.

DETAILED DESCRIPTION

Inasmuch as multiple persons are likely to be wearing lanyards in most academic or institutional facilities, incorporating the capability to use the available lanyard as a proper tourniquet is a valuable resource. A key aspect is "proper"; that is, in accordance with the details of the present invention, a lanyard is configured to include a windlass (i.e., a small, rotatable rod) that may be used to apply the proper amount of pressure to stem the excessive flow of blood without cutting off the supply to extremities.

A tourniquet must be capable of readily terminating a bleeding condition while also not completely stopping the flow of blood to the extreme portions of a limb below the tourniquet away from the injured person's heart. By virtue of including a windlass to achieve a proper amount of pressure, the fixation of the windlass in this position maintains the pressure until further treatment can be rendered.

Figure 1:
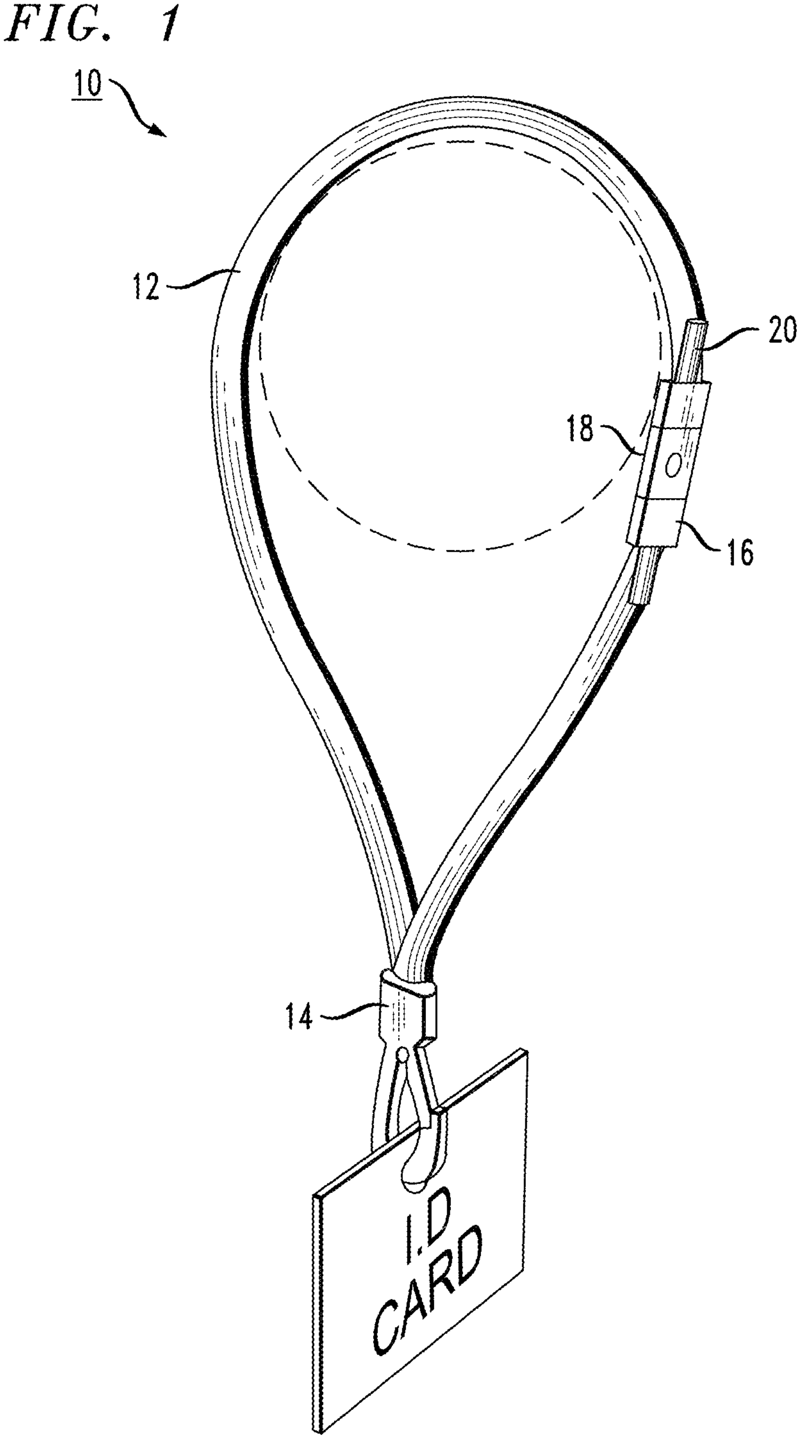
FIG. 1 illustrates an exemplary emergency tourniquet formed in accordance with the teaching of the present invention.

FIG. 1 illustrates an exemplary emergency tourniquet 10 of the present invention, comprising a lanyard 12 formed of a nylon (or similar) material that is strong enough to provide a tightening force when used as a tourniquet. It is to be understood that lanyard 12 may also include some type of "break-away" mechanism (not shown) to prevent its use as a choking instrument in other situations.

Included within lanyard 12 is a clip 14, which is used in a conventional manner to hold an ID (and/or other personal items) in place while being worn, where any type of conventional clip may be used, one example including a carabiner in form. The dotted circle in FIG. 1 is used to illustrate a typical placement of lanyard 12 around an individual's neck. In accordance with the principles of the present invention, emergency tourniquet 10 further comprises an attachment means 16 that is used in combination with a releasable retaining element 18 to support a windlass rod (i.e., a small, rotatable rod) 20. As will be described below, when using emergency tourniquet 10 to control blood flow, included windlass rod 20 is rotated (i.e., wound) in a manner that applies sufficient force of lanyard 12 against an area in proximity to the open wound.

In typical work/school situations where a lanyard is worn, windlass rod 20 may comprise a pen or pointer. Preferably, windlass rod 20 is formed of a stiff (yet lightweight) material that may be rotated (wound) in a known manner to exert force on the tourniquet. Stainless steel is one exemplary material useful for this purpose; aluminum is another choice of a lightweight material suitable for use.

Figure 2:
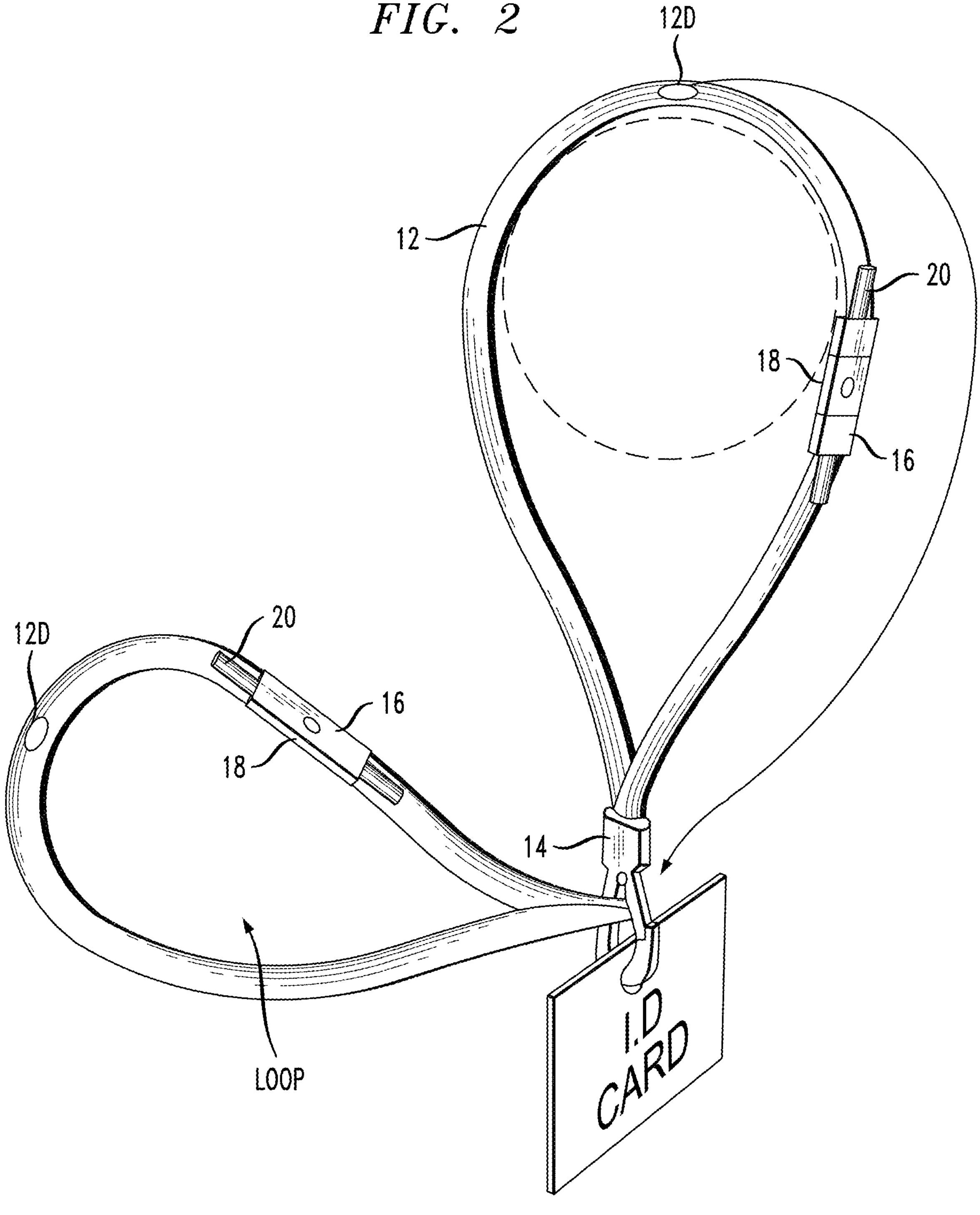
FIG. 2 shows the emergency tourniquet of FIG. 1, indicating an initial step of moving a distal portion of the lanyard through the clip.
Figure 3:
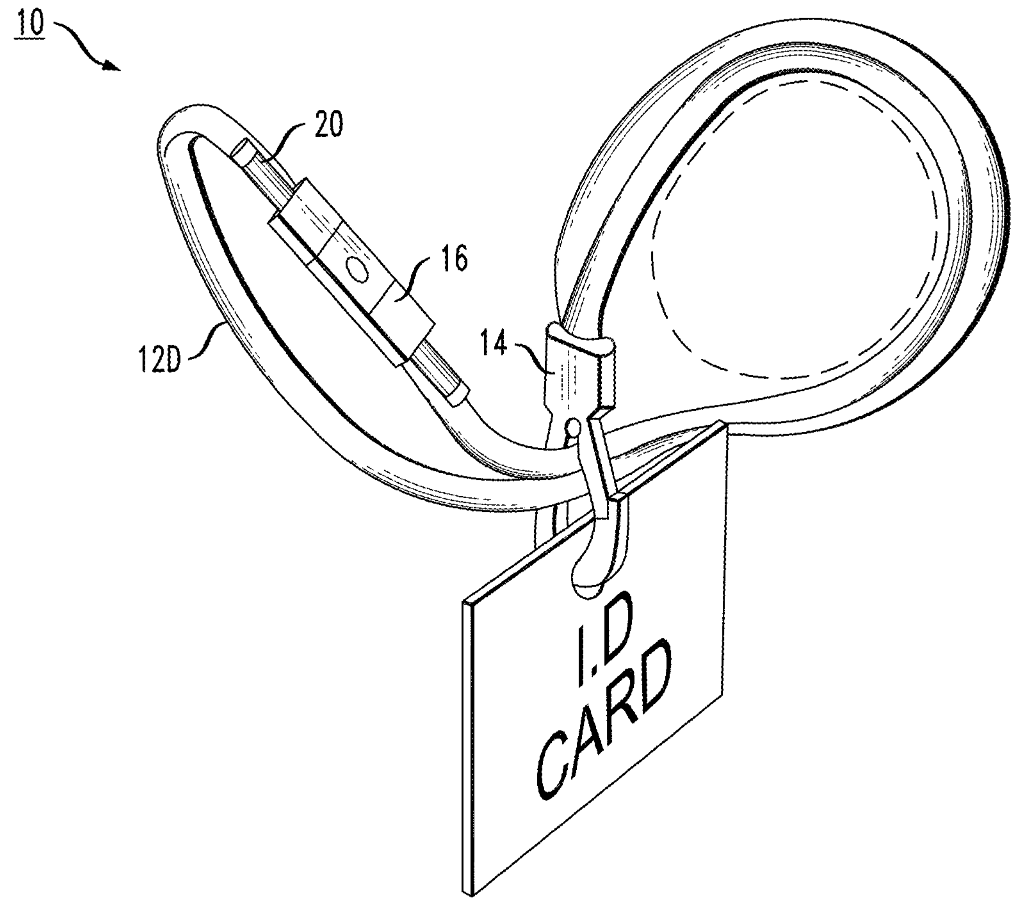
FIG. 3 depicts a loop formed by the lanyard after passing a section through the clip as shown in FIG. 2.

The use of lanyard 12 as a tourniquet is explained with reference to FIGS. 2-6. In a first step, a distal end 12D of lanyard 12 is passed through clip 14, as shown in FIG. 2, to create a loop that is positioned to surround the identified area for tourniquet placement. Distal end 12D is then pulled, as shown in FIG. 3, so that the wound area is completely encircled. Once in place, windlass rod 20 is rotated until a sufficient pressure is applied to stop the bleeding (while not cutting off the complete flow of blood to lower extremities, as mentioned above). Releasable retaining element 18 is then used to cover (surround) windlass rod 20 in its wound position, thus maintaining the application of the desired pressure to slow/prevent further bleeding.

Figure 4:
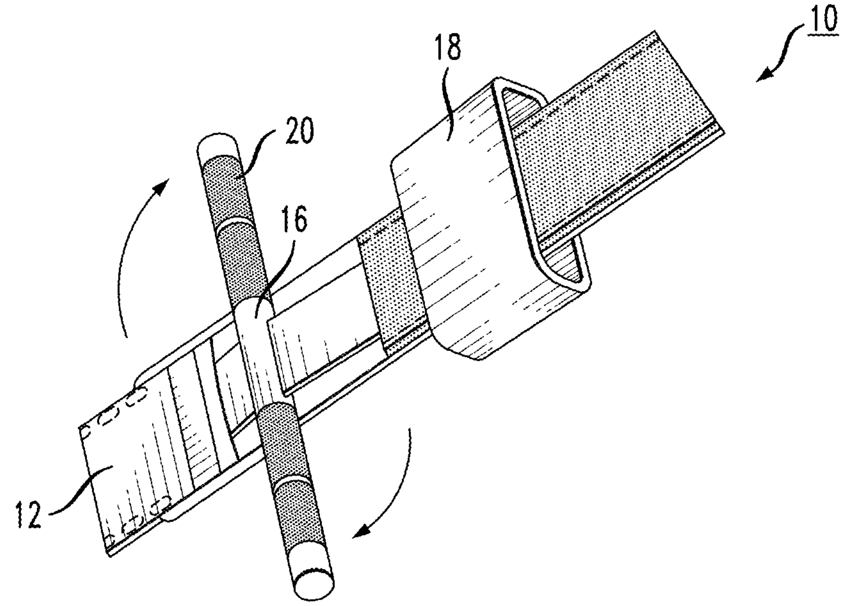
FIG. 4 illustrates an enlarged view of a portion of the emergency tourniquet of FIG. 1, showing in particular the positioning of the windlass rod along a portion of the lanyard, and indicating the capability of the windlass rod to rotate in a manner that tightens the loop around the affected body part.

FIG. 4 is an enlarged view of a portion of emergency tourniquet 10, showing windlass rod 20 as positioned within attachment means 16, with attachment means 16 being an integral element of lanyard 12. In example embodiments, attachment means 16 takes the form of an additional section of nylon (or similar) material that is stitched to an accessible portion of lanyard 12. An opening is formed between the stitched opposing end terminations that is sufficient to allow for windlass rod 20 to pass through (without falling out). Releasable retaining element 18 is also shown in FIG. 4 and may use a well-known type of hook-and-loop attachment configuration to hold windlass rod 20 in place once sufficient pressure has been applied. In particular, the tourniquet force is created by rotating (winding) windlass 20 (as denoted by the arrows) until a sufficient clamping force is applied by lanyard 12 against the wound location.

Figure 5:
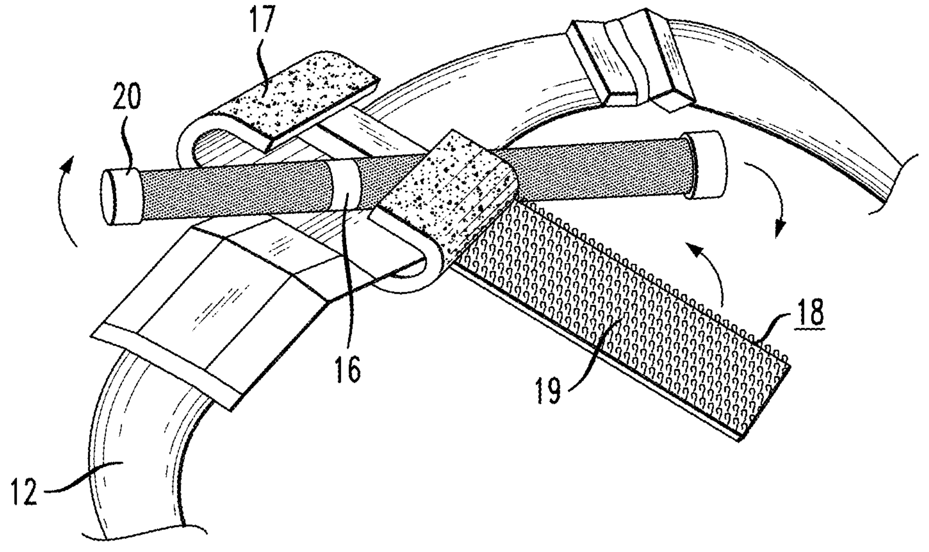
FIG. 5 is a view similar to that of FIG. 4, in this case particularly illustrating an example releasable attachment disposed adjacent to the wound windlass rod.

FIG. 5 is another illustration, similar to FIG. 4, illustrating the use of a rotational movement of windlass rod 20 to tighten lanyard 12 around the wound area. In the embodiment of FIG. 5, releasable retaining element 18 is illustrated to show an example "loop" side 19 that may then cover an associated "hook" side 17 once windlass rod 20 is sufficiently tightened and ensure that the requisite pressure will continue to be applied to the wound area until medical help arrives.

Figure 6:
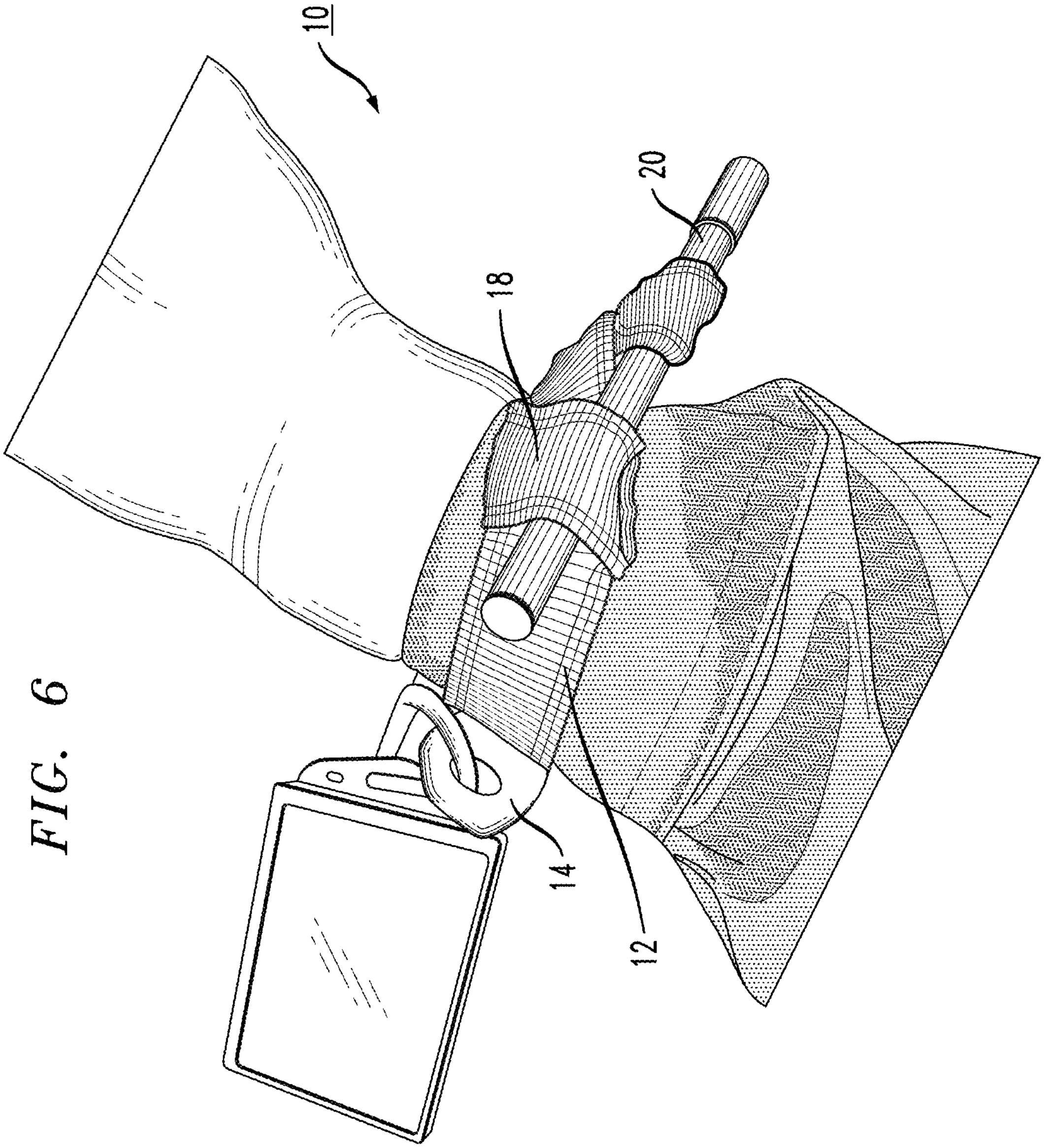
FIG. 6 depicts an exemplary emergency tourniquet of the present invention in a final position of applying pressure to the affected body part.

FIG. 6 depicts an example of emergency tourniquet 10 in its final position in accordance with the principles of the present invention. As mentioned above, in a preferred embodiment, windlass rod 20 may comprise a pen/marker, or the like, which may be used to record the time (perhaps on the ID) when the tourniquet was placed, which is useful information for emergency personnel.

As mentioned above, it is an aspect of the present invention that an individual may be able to apply the tourniquet to their own injury, should the need arise. That is, the simple motions of looping the lanyard through its clip and then rotating the included windlass may be performed with a single hand, if need be. The tourniquet can be self-administered by simply looping one end of the lanyard through the lanyard clip. The windlass rod is applied and designed to tighten the tourniquet by winding. The included strap is used to hold the windless in the "wound" position until emergency personnel arrive.

Summarizing, the inventive emergency tourniquet takes the form of a lanyard (formed of a material such as nylon) that includes a conventional clip (one example clip taking the form of a carabiner) for attachment of identification badges and other accessories (for example, keys). The nylon strap offers superior comfort and strength. In a preferred embodiment, a pen is utilized as the windlass and attached to the lanyard for convenience and to be used as the windlass rod for tightening the tourniquet.

In some example embodiments, the lanyard may include a breakaway mechanism (for example, a hook-and-loop type of configuration) that when pulled abruptly and with force will release, eliminating the chance of someone being choked.

It will be appreciated by those skilled in the art that changes could be made to the embodiments described above without departing from the broad inventive concept thereof. It is understood, therefore, that the presently disclosed technology is not limited to the particular embodiments disclosed, but it is intended to cover modifications within the spirit and scope of the presently disclosed technology as defined by the appended claims.

What is claimed is:

1. An emergency tourniquet, comprising:

a lanyard including a clip member attached thereto;

a windlass rod;

attachment means for securing the windlass rod to a section of the lanyard; and a releasable retaining element disposed on the lanyard in proximity to the windlass rod, wherein for use as a tourniquet a portion of the lanyard, the windlass rod, the attachment means, and the releasable retaining element are configured to pass through the clip member to form a loop so as to be positioned over an injury requiring compression with the windlass rod rotated until a sufficient degree of compression is provided with the releasable retaining element positioned to cover the rotated windlass rod and secure in a manner that maintains the sufficient degree of compression.

2. The emergency tourniquet as defined in claim 1 wherein the windlass rod comprises a metallic rod.

3. The emergency tourniquet as defined in claim 2 wherein the windlass rod comprises a metallic rod selected from the group consisting of a stainless steel rod and an aluminum rod.

4. The emergency tourniquet as defined in claim 1 wherein the windlass rod comprises a writing implement.

5. The emergency tourniquet as defined in claim 4, wherein the emergency tourniquet further comprises a card attached to the clip member for entering incident information regarding use of the emergency tourniquet.

6. The emergency tourniquet as defined in claim 1 wherein the attachment means comprises a section of material permanently affixed to the lanyard in a manner such that the windlass rod passes through an opening between the section of material and the lanyard.

7. The emergency tourniquet as defined in claim 6 wherein the opening between the section of material and the lanyard is about the same as a diameter of the windlass rod.

8. The emergency tourniquet as defined in claim 1, wherein the releasable attachment element comprises a hook-and-loop attachment device.

9. The emergency tourniquet as defined in claim 1, wherein the clip element comprises a carabiner.

10. The emergency tourniquet as defined in claim 1, wherein the lanyard is formed of a nylon strap.

* * * * *